United States Patent
Mignon et al.

(10) Patent No.: US 9,687,057 B2
(45) Date of Patent: Jun. 27, 2017

(54) DYE COMPOSITION USING A SPECIFIC NON-IONIC HYDROTROPIC COMPOUND IN A MEDIUM RICH IN FATTY SUBSTANCES, METHODS AND DEVICE

(71) Applicant: L'OREAL, Paris (FR)

(72) Inventors: Marie Mignon, Paris (FR); Alain Lagrange, Coupvray (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/360,952

(22) PCT Filed: Nov. 28, 2012

(86) PCT No.: PCT/EP2012/073832
§ 371 (c)(1),
(2) Date: May 28, 2014

(87) PCT Pub. No.: WO2013/079527
PCT Pub. Date: Jun. 6, 2013

(65) Prior Publication Data
US 2014/0318566 A1 Oct. 30, 2014

Related U.S. Application Data

(60) Provisional application No. 61/581,169, filed on Dec. 29, 2011.

(30) Foreign Application Priority Data

Nov. 29, 2011 (FR) ..................................... 11 60889

(51) Int. Cl.
| | | |
|---|---|---|
| *A61Q 5/10* | (2006.01) | |
| *A45D 19/02* | (2006.01) | |
| *A61K 8/31* | (2006.01) | |
| *A61K 8/34* | (2006.01) | |
| *A61K 8/39* | (2006.01) | |
| *A61K 8/40* | (2006.01) | |
| *A61K 8/41* | (2006.01) | |
| *A61K 8/60* | (2006.01) | |
| *A61K 8/22* | (2006.01) | |
| *A61K 8/36* | (2006.01) | |
| *A61K 8/96* | (2006.01) | |

(52) U.S. Cl.
CPC ................ *A45D 19/02* (2013.01); *A61K 8/22* (2013.01); *A61K 8/31* (2013.01); *A61K 8/34* (2013.01); *A61K 8/347* (2013.01); *A61K 8/36* (2013.01); *A61K 8/39* (2013.01); *A61K 8/40* (2013.01); *A61K 8/41* (2013.01); *A61K 8/415* (2013.01); *A61K 8/604* (2013.01); *A61K 8/96* (2013.01); *A61Q 5/10* (2013.01); *A45D 2019/025* (2013.01); *A61K 2800/882* (2013.01)

(58) Field of Classification Search
CPC ... A61Q 5/10; A61K 8/31; A61K 8/39; A61K 8/36; A61K 8/347; A61K 8/40; A61K 8/604; A61K 8/34; A61K 8/22; A61K 8/41; A61K 2800/882
USPC ... 8/405, 406, 408, 409, 410, 411, 412, 580, 8/582, 604, 609, 613
See application file for complete search history.

(56) References Cited

U.S. PATENT DOCUMENTS

| | | | |
|---|---|---|---|
| 4,137,180 A | 1/1979 | Naik et al. | |
| 4,874,554 A | 10/1989 | Lange et al. | |
| 7,918,903 B2 | 4/2011 | Audousset et al. | |
| 8,070,831 B2 | 12/2011 | Simonet et al. | |
| 2007/0000074 A1* | 1/2007 | Gross et al. ...................... 8/405 |
| 2007/0099959 A1* | 5/2007 | Pasquier .................. A61K 8/42 514/317 |
| 2010/0154142 A1 | 6/2010 | Audousset et al. | |
| 2010/0162493 A1* | 7/2010 | Audousset et al. ............... 8/416 |
| 2010/0247465 A1 | 9/2010 | Simonet et al. | |
| 2012/0204357 A1 | 8/2012 | Lalleman et al. | |

FOREIGN PATENT DOCUMENTS

| | | |
|---|---|---|
| EP | 2198840 A1 | 6/2010 |
| EP | 2198853 A1 | 6/2010 |
| EP | 2359804 A2 | 8/2011 |
| FR | 2949334 A1 | 3/2011 |
| FR | 2949335 A1 | 3/2011 |
| WO | 2010/070244 A2 | 6/2010 |

OTHER PUBLICATIONS

International Search Report for PCT/EP2012/073832.
Todd, Charles, et al., "Volatile Silicone Fluids for Cosmetic Formulations," Cosmetics and Toiletries, vol. 91, Jan. 1976, pp. 29-32.
Porter, M.R., et al., "Handbook of Surfactants," published by Blackie & Son, (Glasgow and London), 1991, pp. 116-178.
Meylan, William M., et al., "Atom/Fragment Contribution Method for Estimating Octanol-Water Partition Coefficients," Journal of Pharmaceutical Sciences, vol. No. 84, No. 1, Jan. 1995, pp. 83-92.
English language abstract of EP2359804 (Aug. 24, 2011).
English language abstract of FR2949335 (Mar. 5, 2011).
Hansen, Charles M., "Hansen Solubility Parameters: A User's Handbook," CRC Press, 2000, pp. 167-185.
Barton, Allan, F., Handbook of Solubility Parameters and Other Cohension Parameters, CRC Press, Second Edition, 1991, pp. 95-121 and 177-185.

* cited by examiner

*Primary Examiner* — Eisa Elhilo
(74) *Attorney, Agent, or Firm* — The Marbury Law Group, PLLC

(57) ABSTRACT

The present invention relates to a composition for dyeing keratin fibers, comprising at least one fatty substance; at least one surfactant; at least one dye for keratin fibers, having a log P greater than or equal to 1.3; at least one alkaline agent; at least one chemical oxidizing agent; at least 0.5% by weight relative to the weight of the composition of at least one liquid non-ionic compound having a Hansen parameter δ H below 16 MPa ½; the fatty substance content representing in total at least 25% by weight relative to the total weight of the composition. The present invention also relates to a method using this composition, and to multi-compartment devices that are suitable for using this invention.

20 Claims, No Drawings

DYE COMPOSITION USING A SPECIFIC NON-IONIC HYDROTROPIC COMPOUND IN A MEDIUM RICH IN FATTY SUBSTANCES, METHODS AND DEVICE

This is a national stage of International Patent Application No. PCT/EP2012/073832, filed on Nov. 28, 2012, which claims priority to U.S. Provisional Application No. 61/581,169, filed on Dec. 29, 2011, and French Patent Application No. 1160889, filed on Nov. 29, 2011, all of which are incorporated herein by reference in their entireties.

The present invention relates to a composition for dyeing keratin fibres, comprising at least one fatty substance and at least one surfactant, at least one specific hair dye, at least 0.5% by weight of at least one specific non-ionic hydrotropic compound, at least one alkaline agent, at least one chemical oxidizing agent, and the fatty substance content of the composition representing in total at least 25% by weight relative to the total weight of the composition.

The present invention also relates to dyeing methods using this composition, and to a multi-compartment device that is suitable for the use of this composition.

Among the methods for dyeing human keratin fibres, such as hair, mention may be made of oxidative dyeing or permanent dyeing. More particularly, this dyeing method uses one or more oxidative dye precursors and usually one or more oxidation bases optionally combined with one or more couplers.

In general, oxidation bases are chosen from ortho- or para-phenylenediamines, ortho- or para-aminophenols and heterocyclic compounds. These oxidation bases are colourless or weakly coloured compounds which, in combination with oxidizing products, provide access to coloured species by a method of oxidative condensation.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colours to be obtained.

Direct dyeing or semi-permanent dyeing is also known. The method conventionally used for direct dyeing consists in applying direct dyes to the keratin fibres, said dyes being coloured and colouring molecules that have an affinity for the fibres, and then leaving them to take, to allow the molecules to penetrate by diffusion to the interior of the fibre, and then rinsing the fibres.

The direct dyes generally used are chosen from nitrobenzene, anthraquinone, nitropyridine, azo, methine, azomethine, xanthene, acridine, azine and triarylmethane direct dyes.

This type of method does not require the use of an oxidizing agent to develop the colour. However, it is not excluded to use one in order to obtain, along with the colouring, a lightening effect. Such a method is then referred to as direct dyeing or semi-permanent dyeing under lightening conditions.

Methods for permanent dyeing or semi-permanent dyeing under lightening conditions thus consist in using, along with the dye composition, an aqueous composition comprising at least one oxidizing agent, under alkaline pH conditions in the vast majority of cases. The role of this oxidizing agent is to degrade the melanin of the hair, which, depending on the nature of the oxidizing agent present, leads to more or less pronounced lightening of the fibres. Thus, for relatively weak lightening, the oxidizing agent is generally hydrogen peroxide. When more substantial lightening is desired, peroxygenated salts, for instance persulfates, are usually used in the presence of hydrogen peroxide.

The colouring methods are usually implemented under alkaline conditions; the alkaline agent both activates the oxidizing agent and facilitates uptake of the dyes, by causing the scales on the fibres to open. Conventionally, the alkaline agent used is ammonia. It is very effective but presents many drawbacks due to its high volatility, its strong and unpleasant odour and risks of intolerance (irritation, tingling) that it may cause.

Attempts to replace ammonia in part or completely by one or more other conventional alkaline agents have not led to compositions that are as effective in terms of colouring results.

Recently, dye compositions rich in fatty substances have been proposed, obtained by mixing two or three compositions and comprising inter alia a fatty substance.

These compositions make it possible to reduce the ammonia content or even to remove it completely while retaining colouring levels at least as high as with conventional compositions comprising high concentrations of this alkaline agent.

However, even in these conditions, the results obtained are not optimum, in particular in terms of intensity and/or chromaticity. This is the case for hydrophobic dyes in particular.

One of the objectives of the present invention is to propose compositions for dyeing human keratin fibres such as the hair that do not have the drawbacks of existing compositions.

In particular, the composition according to the invention makes it possible to obtain colours that are satisfactory, especially in terms of intensity and coverage or uptake of the colour at the root of the hair, which makes it possible to avoid a "root" effect with the colouring.

It is also possible to obtain colours that are very stable towards light.

In addition, the invention makes it possible to achieve substantial degrees of lightening while at the same time colouring, without using persalts or increasing the amount of chemical oxidizing agent or of alkaline agent.

These aims and others are achieved by the present invention, which thus relates to a composition for dyeing keratin fibres, in particular human keratin fibres such as the hair, comprising:
- at least one fatty substance,
- at least one surfactant,
- at least one dye for keratin fibres, having a log P greater than or equal to 1.3,
- at least one alkaline agent,
- at least one chemical oxidizing agent,
- at least 0.5% by weight of at least one liquid non-ionic compound having a Hansen parameter δH below 16 MPa½,
- the fatty substance content representing in total at least 25% by weight relative to the total weight of the composition.

The invention also relates to a dyeing method using the composition of the invention, and multi-compartment devices that enable the use of the composition of the invention.

Thus, using the dyeing composition according to the invention leads to powerful, intense, chromatic and, moreover, sparingly selective colouring, i.e. colouring that is uniform along the fibre.

The invention also makes it possible to cover keratin fibres particularly well at their root, especially down to three centimeters from the base of said fibres.

Moreover, the colours obtained after treating the fibres remain stable, in particular towards light.

The invention also makes it possible to reduce the amounts of active agents of the invention such as the dyes and/or alkaline agents and/or oxidizing agents without the composition losing dyeing efficacy.

Furthermore, the methods according to the invention make it possible to use formulations that are less malodorous when they are applied to the hair or being prepared.

Other characteristics and advantages of the invention will emerge more clearly on reading the description and the examples that follow.

In that which will follow and unless otherwise indicated, the limits of a range of values are included within this range.

The human keratin fibres treated by the method according to the invention are preferably the hair.

The expression "at least one" is equivalent to the expression "one or more".

Fatty Substances:

As has been mentioned, the composition of the invention comprises one or more fatty substances.

The term "fatty substance" is understood to mean an organic compound which is insoluble in water at ordinary temperature (25° C.) and at atmospheric pressure (760 mmHg) (solubility of less than 5%, preferably of less than 1% and more preferably still of less than 0.1%). They exhibit, in their structure, at least one hydrocarbon chain comprising at least 6 carbon atoms or a sequence of at least two siloxane groups. In addition, fatty substances are generally soluble in organic solvents under the same temperature and pressure conditions, such as, for example, chloroform, dichloromethane, carbon tetrachloride, ethanol, benzene, toluene, tetrahydrofuran (THF), liquid petrolatum or decamethylcyclopentasiloxane.

Preferably, the fatty substances of the invention do not comprise salified or unsalified carboxylic acid groups (COOH or COO$^-$). In particular, the fatty substances of the invention are neither polyoxyalkylenated nor polyglycerolated.

The term "oil" is understood to mean a "fatty substance" that is liquid at room temperature (25° C.) and at atmospheric pressure (760 mmHg).

The term "non-silicone oil" is understood to mean an oil not comprising a silicon (Si) atom and the term "silicone oil" is understood to mean an oil comprising at least one silicon atom.

More particularly, the fatty substances are chosen from $C_6$-$C_{16}$ hydrocarbons, hydrocarbons comprising more than 16 carbon atoms, non-silicone oils of animal origin, vegetable oils of triglyceride type, synthetic triglycerides, fluorinated oils, fatty alcohols, fatty acid and/or fatty alcohol esters other than the triglycerides and vegetable waxes, non-silicone waxes, silicones.

It should be remembered that, within the meaning of the invention, fatty alcohols, esters and acids more particularly exhibit at least one saturated or unsaturated and linear or branched hydrocarbon group which comprises from 6 to 30 carbon atoms and which is optionally substituted, in particular by one or more hydroxyl groups (in particular 1 to 4). If they are unsaturated, these compounds can comprise from one to three conjugated or non-conjugated carbon-carbon double bonds.

As regards the $C_6$-$C_{16}$ hydrocarbons, they are linear, branched or optionally cyclic, and are preferably alkanes.

Mention may be made, by way of example, of hexane, dodecane or isoparaffins, such as isohexadecane or isodecane.

Mention may be made, as hydrocarbon oils of animal origin, of perhydrosqualene.

The triglyceride oils of vegetable or synthetic origin are preferably chosen from liquid triglycerides of fatty acids comprising from 6 to 30 carbon atoms, such as heptanoic or octanoic acid triglycerides, or alternatively, for example, sunflower oil, maize oil, soybean oil, cucumber oil, grape seed oil, sesame oil, hazelnut oil, apricot oil, macadamia oil, arara oil, castor oil, avocado oil, caprylic/capric acid triglycerides, such as those sold by Stéarineries Dubois or those sold under the names Miglyol® 810, 812 and 818 by Dynamit Nobel, jojoba oil or shea butter oil.

The linear or branched hydrocarbons of mineral or synthetic origin having more than 16 carbon atoms are preferably chosen from liquid paraffins, petrolatum, liquid petrolatum, polydecenes or hydrogenated polyisobutene, such as Parleam®.

The fluorinated oils can be chosen from perfluoromethylcyclopentane and perfluoro-1,3-dimethylcyclohexane, sold under the names Flutec® PC1 and Flutec® PC3 by BNFL Fluorochemicals; perfluoro-1,2-dimethylcyclobutane; perfluoroalkanes, such as dodecafluoropentane and tetradecafluorohexane, sold under the names PF 5050® and PF 5060® by 3M, or bromoperfluorooctyl, sold under the name Foralkyl® by Atochem; nonafluoromethoxybutane and nonafluoroethoxyisobutane; or perfluoromorpholine derivatives, such as 4-(trifluoromethyl)perfluoromorpholine, sold under the name PF 5052® by 3M.

The fatty alcohols which are suitable for the implementation of the invention are more particularly chosen from saturated or unsaturated and linear or branched alcohols comprising from 6 to 30 carbon atoms and preferably from 8 to 30 carbon atoms. Mention may be made, for example, of cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol.

As regards the esters of a fatty acid and/or of a fatty alcohol, which are advantageously different from the triglycerides mentioned above, mention may be made especially of esters of saturated or unsaturated and linear or branched $C_1$-$C_{26}$ aliphatic monoacids or polyacids and of saturated or unsaturated and linear or branched $C_1$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates; 2-ethylhexyl palmitate; 2-octyldecyl palmitate; alkyl myristates, such as isopropyl, butyl, cetyl, 2-octyldodecyl, myristyl or stearyl myristate; hexyl stearate; butyl stearate; isobutyl stearate; dioctyl malate; hexyl laurate or 2-hexyldecyl laurate.

Still within the context of this alternative form, use may also be made of esters of $C_4$-$C_{22}$ di- or tricarboxylic acids and of $C_1$-$C_{22}$ alcohols and esters of mono-, di- or tricarboxylic acids and of di-, tri-, tetra- or pentahydroxy $C_2$-$C_{26}$ alcohols.

Mention may in particular be made of: diethyl sebacate; diisopropyl sebacate; diisopropyl adipate; di(n-propyl)adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition can also comprise, as fatty ester, sugar esters and diesters of $C_6$-$C_{30}$ and preferably $C_{12}$-$C_{22}$ fatty acids. It should be remembered that the term "sugar" is understood to mean oxygen-comprising hydrocarbon compounds which have several alcohol functional groups, with or without aldehyde or ketone functional groups, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose, lactose and their derivatives, in particular alkyl derivatives, such as methyl derivatives, for example methylglucose.

The esters of sugars and of fatty acids can be chosen in particular from the group consisting of the esters or mixtures of esters of sugars described above and of saturated or unsaturated and linear or branched $C_6$-$C_{30}$ and preferably $C_{12}$-$C_{22}$ fatty acids. If they are unsaturated, these compounds can comprise from one to three conjugated or non-conjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates or their mixtures, such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose.

Mention may be made, by way of example, of the product sold under the name Glucate® DO by Amerchol, which is a methylglucose dioleate.

Mention may also be made, by way of examples of esters or mixtures of esters of sugar and of fatty acid, of:
the products sold under the names F160, F140, F110, F90, F70 and SL40 by Crodesta, respectively denoting sucrose palmitate/stearates formed of 73% monoester and 27% di- and triester, of 61% monoester and 39% di-, tri- and tetraester, of 52% monoester and 48% di-, tri- and tetraester, of 45% monoester and 55% di-, tri- and tetraester, and of 39% monoester and 61% di-, tri- and tetraester, and sucrose monolaurate;
the products sold under the name Ryoto Sugar Esters, for example referenced B370 and corresponding to sucrose behenate formed of 20% monoester and 80% diester, triester and polyester;
the sucrose monopalmitate/stearate-dipalmitate/stearate sold by Goldschmidt under the name Tegosoft® PSE.

The non-silicone wax(es) are chosen in particular from carnauba wax, candelilla wax, esparto wax, paraffin wax, ozokerite, vegetable waxes, such as olive tree wax, rice wax, hydrogenated jojoba wax or absolute flower waxes, such as the blackcurrant blossom essential wax sold by Bertin (France), or animal waxes, such as beeswaxes or modified beeswaxes (cerabellina); other waxes or waxy starting materials which can be used according to the invention are in particular marine waxes, such as that sold by Sophim under the reference M82, polyethylene waxes or polyolefin waxes in general.

The silicones which can be used in the cosmetic compositions of the present invention are volatile or non-volatile and cyclic, linear or branched silicones, which are unmodified or modified by organic groups, having a viscosity from $5\times10^{-6}$ to 2.5 m$^2$/s at 25° C. and preferably from $1\times10^{-5}$ to 1 m$^2$/s.

The silicones which can be used in accordance with the invention can be provided in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups and alkoxy groups.

Organopolysiloxanes are defined in more detail in Walter Noll's publication "Chemistry and Technology of Silicones" (1968), Academic Press. They can be volatile or non-volatile.

When they are volatile, the silicones are more particularly chosen from those having a boiling point of between 60° C. and 260° C., and more particularly still from:
(i) cyclic polydialkylsiloxanes comprising from 3 to 7 and preferably from 4 to 5 silicon atoms. They are, for example, octamethylcyclotetrasiloxane, sold in particular under the name Volatile Silicone® 7207 by Union Carbide or Silbione® 70045 V2 by Rhodia, decamethylcyclopentasiloxane, sold under the name Volatile Silicone® 7158 by Union Carbide and Silbione® 70045 V5 by Rhodia, and their mixtures.

Mention may also be made of cyclocopolymers of the dimethylsiloxane/methylalkylsiloxane type, such as Volatile Silicone® FZ 3109, sold by Union Carbide, having the formula:

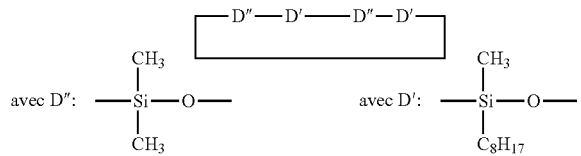

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-1,1'-bis(2,2,2', 2',3,3'-hexatrimethylsilyloxy)neopentane;

(ii) volatile linear polydialkylsiloxanes having from 2 to 9 silicon atoms and exhibiting a viscosity of less than or equal to $5 \times 10^{-6}$ m$^2$/s at 25° C. An example is decamethyltetrasiloxane, sold in particular under the name SH 200 by Toray Silicone. Silicones coming within this category are also described in the paper published in Cosmetics and Toiletries, Vol. 91, January 1976, pp. 27-32, Todd & Byers, "Volatile Silicone Fluids for Cosmetics".

Use is preferably made of non-volatile polydialkylsiloxanes, of polydialkylsiloxane gums and resins, of polyorganosiloxanes modified by the above organofunctional groups, and of their mixtures.

These silicones are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without implied limitation, of the following commercial products:
- the Silbione® oils of the 47 and 70 047 series or the Mirasil® oils sold by Rhodia, such as, for example, the oil 70 047 V 500 000;
- the oils of the Mirasil® series sold by Rhodia;
- the oils of the 200 series from Dow Corning, such as DC200 having a viscosity of 60000 mm$^2$/s;
- the Viscasil® oils from General Electric and certain oils of the SF series (SF 96, SF 18) from General Electric.

Mention may also be made of polydimethylsiloxanes having dimethylsilanol end groups known under the name of dimethiconol (CTFA), such as the oils of the 48 series from Rhodia.

Mention may also be made, in this category of polydialkylsiloxanes, of the products sold under the names Abil Wax® 9800 and 9801 by Goldschmidt, which are polydi (C$_1$-C$_{20}$)alkylsiloxanes.

The silicone gums which can be used in accordance with the invention are in particular polydialkylsiloxanes and preferably polydimethylsiloxanes having high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or their mixtures.

Products which can be used more particularly in accordance with the invention are mixtures, such as:
- the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by Dow Corning;
- the mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;
- the mixtures of two PDMSs with different viscosities, and more particularly of a PDMS gum and a PDMS oil, such as the product SF 1236 from General Electric. The product SF 1236 is the mixture of a gum SE 30 defined above having a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins which can be used in accordance with the invention are crosslinked siloxane systems including the following units:

$R_2SiO_{2/2}$, $R_3SiO_{1/2}$, $RSiO_{3/2}$ and $SiO_{4/2}$ in which R represents an alkyl having from 1 to 16 carbon atoms. Among these products, those which are particularly preferred are those in which R denotes a lower $C_1$-$C_4$ alkyl group, more particularly methyl.

Mention may be made, among these resins, of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type, sold in particular under the names X22-4914, X21-5034 and X21-5037 by Shin-Etsu.

The organomodified silicones which can be used in accordance with the invention are silicones as defined above comprising, in their structure, one or more organofunctional groups attached via a hydrocarbon group.

In addition to the silicones described above, the organomodified silicones can be polydiarylsiloxanes, in particular polydiphenylsiloxanes, and polyalkylarylsiloxanes functionalized by the abovementioned organofunctional groups.

The polyalkylarylsiloxanes are chosen in particular from linear and/or branched polydimethyl/methylphenylsiloxanes and polydimethyl/diphenylsiloxanes with a viscosity ranging from $1 \times 10^{-6}$ to $5 \times 10^{-2}$ m$^2$/s at 25° C.

Mention may be made, among these polyalkylarylsiloxanes, by way of example, of the products sold under the following names:
- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Mention may be made, among the organomodified silicones, of polyorganosiloxanes comprising:
- substituted or unsubstituted amino groups, such as the products sold under the names GP 4 Silicone Fluid and GP 7100 by Genesee or the products sold under the names Q2 8220 and Dow Corning 929 or 939 by Dow Corning. The substituted amino groups are in particular $C_1$-$C_4$ aminoalkyl groups;
- alkoxylated groups, such as the product sold under the name Silicone Copolymer F-755 by SWS Silicones, and Abil Wax® 2428, 2434 and 2440 by Goldschmidt.

More particularly, the fatty substances are chosen from compounds that are liquid or pasty at room temperature (25° C.) and at atmospheric pressure.

Preferably, the fatty substance is a compound which is liquid at a temperature of 25° C. and at atmospheric pressure.

The fatty substances are advantageously chosen from $C_6$-$C_{16}$ hydrocarbons, hydrocarbons having more than 16 carbon atoms, triglycerides, fatty alcohols, fatty acid and/or fatty alcohol esters other than the triglycerides, silicones or their mixtures.

Preferably, the fatty substance is chosen from liquid petrolatum, $C_6$-$C_{16}$ alkanes, polydecenes, liquid fatty acid and/or fatty alcohol esters, liquid fatty alcohols or their mixtures.

Better still, the fatty substance is chosen from liquid petrolatum, $C_6$-$C_{16}$ alkanes or polydecenes.

The composition according to the invention comprises at least 25% by weight of fatty substances.

The composition according to the invention more particularly exhibits a fatty substance content ranging from 25% to 80% by weight, preferably from 30% to 70% by weight and more advantageously still from 30% to 60% by weight, relative to the weight of the composition.

Surfactants:

The composition of the invention also comprises one or more surfactants.

In particular, any surfactants are chosen from anionic, amphoteric, zwitterionic, cationic or non-ionic surfactants, and preferentially non-ionic surfactants.

The term "anionic surfactant" is understood to mean a surfactant comprising, as ionic or ionizable groups, only anionic groups. These anionic groups are preferably chosen from the groups —C(O)OH, —C(O)O⁻, —SO₃H, —S(O)₂O⁻, —OS(O)₂OH, —OS(O)₂O⁻, —P(O)OH₂, —P(O)₂O⁻, —P(O)O₂⁻, —P(OH)₂, —P(O)OH, —P(OH)O⁻, =P(O)O⁻, =POH, =PO⁻, the anionic parts comprising a cationic counterion such as an alkali metal, an alkaline-earth metal or an ammonium.

Mention may be made, as examples of anionic surfactants that can be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates, salts of alkyl monoesters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids; and the corresponding non-salified forms of all these compounds, the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, it (they) may be chosen from alkali metal salts such as the sodium or potassium salt and preferably the sodium salt, ammonium salts, amine salts and in particular aminoalcohol salts, or alkaline earth metal salts such as the magnesium salts.

Examples of aminoalcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline earth metal salts and in particular of the sodium or magnesium salts.

Use is preferably made, among the anionic surfactants mentioned, of ($C_6$-$C_{24}$)alkyl sulfates, ($C_6$-$C_{24}$)alkyl ether sulfates comprising from 2 to 50 ethylene oxide units, in particular in the form of alkali metal, ammonium, aminoalcohol and alkaline earth metal salts, or a mixture of these compounds.

In particular, it is preferable to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, aminoalcohol and alkaline earth metal salts, or a mixture of these compounds. Better still, it is preferable to use sodium lauryl ether sulfate comprising 2.2 mol of ethylene oxide.

The amphoteric or zwitterionic surfactant(s), which is (are) preferably (a) non-silicone surfactant(s), which can be used in the present invention can in particular be derivatives of optionally quaternized secondary or tertiary aliphatic amines, in which derivatives the aliphatic group is a linear or branched chain comprising from 8 to 22 carbon atoms, said amine derivatives comprising at least one anionic group, such as, for example, a carboxylate, sulfonate, sulfate, phosphate or phosphonate group. Mention may in particular be made of ($C_8$-$C_{20}$)alkyl betaines, sulfobetaines, ($C_8$-$C_{20}$)alkylamido($C_3$-$C_8$)alkyl betaines and ($C_8$-$C_{20}$)alkylamido($C_6$-$C_8$)alkyl sulfobetaines.

Mention may also be made, among the optionally quaternized secondary or tertiary aliphatic amine derivatives which can be used, as defined above, of the compounds having the following respective structures (A1) and (A2):

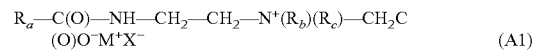

$$R_a\text{—}C(O)\text{—}NH\text{—}CH_2\text{—}CH_2\text{—}N^+(R_b)(R_c)\text{—}CH_2C(O)O^-M^+X^- \quad (A1)$$

in which formula (A1):

$R_a$ represents a $C_{10}$-$C_{30}$ alkyl or alkenyl group derived from an acid $R_a$COOH preferably present in hydrolyzed coconut oil, or a heptyl, nonyl or undecyl group;

$R_b$ represents a β-hydroxyethyl group; and $R_c$ represents a carboxymethyl group;

$M^+$ represents a cationic counterion derived from an alkali metal or alkaline earth metal, such as sodium, an ammonium ion or an ion resulting from an organic amine, and $X^-$ represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate; or alternatively $M^+$ and $X^-$ are absent;

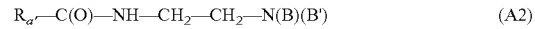

$$R_{a'}\text{—}C(O)\text{—}NH\text{—}CH_2\text{—}CH_2\text{—}N(B)(B') \quad (A2)$$

in which formula (A2):

B represents the group —CH₂—CH₂—O—X';

B' represents the group —(CH₂)_zY', with z=1 or 2;

X' represents the group —CH₂—C(O)OH, —CH₂—C(O)OZ', —CH₂—CH₂—C(O)OH or —CH₂—CH₂—C(O)OZ', or a hydrogen atom;

Y' represents the group —C(O)OH, —C(O)OZ' or —CH₂—CH(OH)—SO₃H or the group —CH₂—CH(OH)—SO₃—Z';

Z' represents a cationic counterion resulting from an alkali metal or alkaline earth metal, such as sodium, an ammonium ion or an ion resulting from an organic amine;

$R_{a'}$ represents a $C_{10}$-$C_{30}$ alkyl or alkenyl group of an acid $R_{a'}$—C(O)OH preferably present in hydrolyzed linseed oil or coconut oil, an alkyl group, in particular a $C_{17}$ alkyl group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

Mention may be made, by way of example, of the cocoamphodiacetate sold by Rhodia under the trade name Miranol® C2M Concentrate.

Among the abovementioned amphoteric or zwitterionic surfactants, use is preferably made of ($C_8$-$C_{20}$)alkyl betaines, such as coco betaine, or ($C_8$-$C_{20}$)alkylamido($C_3$-$C_8$)alkyl betaines, such as cocamidopropyl betaine, and their mixtures. More preferably, the amphoteric or zwitterionic surfactant(s) are chosen from cocamidopropyl betaine and coco betaine.

The cationic surfactant(s) which can be used in the composition according to the invention comprise, for example, salts of optionally polyoxyalkylenated primary, secondary or tertiary fatty amines, quaternary ammonium salts, and their mixtures.

Examples of quaternary ammonium salts that may especially be mentioned include:

those corresponding to the general formula (A3) below:

in which formula (A3):
$R_8$ to $R_{11}$, which are identical or different, represent a linear or branched aliphatic group comprising from 1 to 30 carbon atoms, or an aromatic group, such as aryl or alkylaryl, it being understood that at least one of the groups $R_8$ to $R_{11}$ comprises from 8 to 30 carbon atoms and preferably from 12 to 24 carbon atoms; and $X^-$ represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$) alkylarylsulfonates, in particular methyl sulfate and ethyl sulfate.

The aliphatic groups of $R_8$ to $R_{11}$ may also comprise heteroatoms, especially such as oxygen, nitrogen, sulfur and halogens.

The aliphatic groups of $R_8$ to $R_{11}$ are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and hydroxy($C_1$-$C_{30}$)alkyl groups, and $X^-$ is an anionic counterion chosen from halides, phosphates, acetates, lactates, ($C_1$-$C_4$)alkyl sulfates, or ($C_1$-$C_4$)alkyl- or ($C_1$-$C_4$)alkylarylsulfonates.

Preference is given, among the quaternary ammonium salts having the formula (A3), firstly to tetraalkylammonium chlorides, such as, for example, dialkyldimethylammonium or alkyltrimethylammonium chlorides in which the alkyl group includes approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by Van Dyk;

quaternary ammonium salts of imidazoline, for instance those having the following formula (A4):

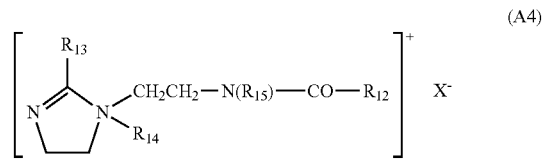

in which formula (A4):
$R_{12}$ represents an alkenyl or alkyl group comprising from 8 to 30 carbon atoms, for example tallow fatty acid derivatives;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ represents an organic or inorganic anionic counterion, such as that chosen from halides, phosphates, acetates, lactates, ($C_1$-$C_4$)alkyl sulfates, or ($C_1$-$C_4$)alkyl- or ($C_1$-$C_4$)alkylarylsulfonates.

$R_{12}$ and $R_{13}$ preferably denote a mixture of alkenyl or alkyl groups comprising from 12 to 21 carbon atoms, for example tallow fatty acid derivatives, $R_{14}$ denotes a methyl group and $R_{15}$ denotes a hydrogen atom. Such a product is sold, for example, under the name Rewoquat® W 75 by the company Rewo;

di- or triquaternary ammonium salts, in particular having the following formula (A5):

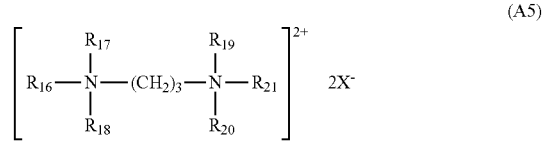

in which formula (A5):
$R_{16}$ denotes an alkyl group comprising approximately from 16 to 30 carbon atoms, which is optionally hydroxylated and/or interrupted by one or more oxygen atoms;

$R_{17}$ is chosen from hydrogen, an alkyl group comprising from 1 to 4 carbon atoms or a —($CH_2$)$_3$—$N^+$($R_{16a}$)($R_{17a}$)($R_{18a}$)$X^-$ group;

$R_{16a}$, $R_{17a}$, $R_{18a}$, $R_{18}$, $R_{19}$, $R_{20}$ and $R_{21}$, which are identical or different, are chosen from hydrogen and an alkyl group comprising from 1 to 4 carbon atoms; and $X^-$, which are identical or different, represent an organic or inorganic anionic counterion, such as that chosen from halides, acetates, phosphates, nitrates, ($C_1$-$C_4$) alkyl sulfates, or ($C_1$-$C_4$)alkyl- or ($C_1$-$C_4$)alkylarylsulfonates, in particular methyl sulfate and ethyl sulfate.

Such compounds are, for example, Finquat CT-P, provided by Finetex (Quaternium 89), or Finquat CT, provided by Finetex (Quaternium 75);

quaternary ammonium salts comprising one or more ester functional groups, such as those of following formula (A6):

(A6)

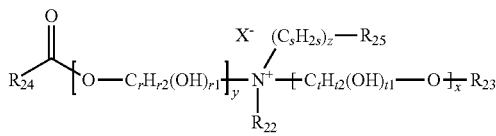

in which formula (A6):
R$_{22}$ is chosen from C$_1$-C$_6$ alkyl groups and C$_1$-C$_6$ hydroxyalkyl or dihydroxyalkyl groups,
R$_{23}$ is chosen from:
the group

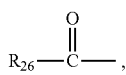

linear or branched, saturated or unsaturated C$_1$-C$_{22}$ hydrocarbon groups R$_{27}$,
a hydrogen atom,
R$_{25}$ is chosen from:
the group

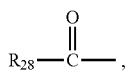

linear or branched, saturated or unsaturated C$_1$-C$_6$ hydrocarbon groups R$_{29}$,
a hydrogen atom,
R$_{24}$, R$_{26}$ and R$_{28}$, which are identical or different, are chosen from saturated or unsaturated and linear or branched C$_7$-C$_{21}$ hydrocarbon groups;
r, s and t, which are identical or different, are integers having values from 2 to 6,
r1 and t1, which are identical or different, have the value 0 or 1, with r2+r1=2r and t1+t2=2t,
y is an integer having a value from 1 to 10,
x and z, which are identical or different, are integers having values from 0 to 10,
X$^-$ represents an organic or inorganic anionic counterion, with the proviso that the sum x+y+z has a value from 1 to 15, that, when x has the value 0, then R$_{23}$ denotes R$_{27}$ and that, when z has the value 0, then R$_{25}$ denotes R$_{29}$.

The alkyl groups R$_{22}$ can be linear or branched and more particularly linear.

Preferably, R$_{22}$ denotes a methyl, ethyl, hydroxyethyl or dihydroxypropyl group and more particularly a methyl or ethyl group.

Advantageously, the sum x+y+z has a value from 1 to 10.

When R$_{23}$ is a hydrocarbon group R$_{27}$, it can be long and have from 12 to 22 carbon atoms or can be short and have from 1 to 3 carbon atoms.

When R$_{25}$ is a hydrocarbon group R$_{29}$, it preferably has from 1 to 3 carbon atoms.

Advantageously, R$_{24}$, R$_{26}$ and R$_{28}$, which are identical or different, are chosen from saturated or unsaturated and linear or branched C$_{11}$-C$_{21}$ hydrocarbon groups and more particularly from saturated or unsaturated and linear or branched C$_{11}$-C$_{21}$ alkyl and alkenyl groups.

Preferably, x and z, which are identical or different, have the value 0 or 1.

Advantageously, y is equal to 1.

Preferably, r, s and t, which are identical or different, have the value 2 or 3 and more particularly still are equal to 2.

The anionic counterion X$^-$ is preferably a halide, such as chloride, bromide or iodide; a (C$_1$-C$_4$)alkyl sulfate; or a (C$_1$-C$_4$)alkyl- or (C$_1$-C$_4$)alkylarylsulfonate. However, it is possible to use methanesulfonate, phosphate, nitrate, tosylate, an anion derived from an organic acid, such as acetate or lactate, or any other anion compatible with the ammonium comprising an ester functional group.

The anionic counterion X$^-$ is more particularly still chloride, methyl sulfate or ethyl sulfate.

Use is more particularly made, in the composition according to the invention, of the ammonium salts having the formula (A6), in which:
R$_{22}$ denotes a methyl or ethyl group,
x and y are equal to 1,
z is equal to 0 or 1,
r, s and t are equal to 2,
R$_{23}$ is chosen from:
the group

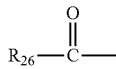

methyl, ethyl or C$_{14}$-C$_{22}$ hydrocarbon groups,
a hydrogen atom,
R$_{25}$ is chosen from:
the group

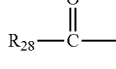

a hydrogen atom,
R$_{24}$, R$_{26}$ and R$_{28}$, which are identical or different, are chosen from saturated or unsaturated and linear or branched C$_{13}$-C$_{17}$ hydrocarbon groups and preferably from saturated or unsaturated and linear or branched C$_{13}$-C$_{17}$ alkyl and alkenyl groups.

Advantageously, the hydrocarbon radicals are linear.

Among the compounds having the formula (A6), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and their mixtures. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of their methyl esters. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester functional group that are described in U.S. Pat. No. 4,874,554 and U.S. Pat. No. 4,137,180.

Use may be made of behenoylhydroxypropyltrimethylammonium chloride, provided by Kao under the name Quatarmin BTC 131.

Preferably, the ammonium salts containing at least one ester functional group contain two ester functional groups.

Among the cationic surfactants that may be present in the composition according to the invention, it is more particularly preferred to choose cetyltrimethylammonium, behenyltrimethylammonium and dipalmitoylethylhydroxyethylmethylammonium salts, and their mixtures, and more particularly behenyltrimethylammonium chloride, cetyltrimethylammonium chloride and dipalmitoylethylhydroxyethylammonium methosulfate, and their mixtures.

Examples of non-ionic surfactants that can be used in the composition used according to the invention are described, for example, in the "Handbook of Surfactants" by M. R. Porter, published by Blackie & Son (Glasgow and London), 1991, pp. 116-178. They are especially chosen from alcohols, α-diols and $(C_1-C_{20})$alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50 and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, optionally oxyalkylenated alkyl polyglycosides, alkyl glucoside esters, derivatives of N-alkylglucamine and of N-acylmethylglucamine, aldobionamides and amine oxides.

The non-ionic surfactants are chosen more particularly from mono- or polyoxyalkylenated or mono- or polyglycerolated non-ionic surfactants. The oxyalkylene units are more particularly oxyethylene or oxypropylene units, or their combination, preferably oxyethylene units.

Mention may be made, as examples of oxyalkylenated non-ionic surfactants, of:
 oxyalkylenated $(C_8-C_{24})$alkylphenols;
 saturated or unsaturated and linear or branched oxyalkylenated $C_8-C_{30}$ alcohols;
 saturated or unsaturated and linear or branched oxyalkylenated $C_8-C_{30}$ amides;
 esters of saturated or unsaturated and linear or branched $C_8-C_{30}$ acids and of polyethylene glycols;
 polyoxyethylenated esters of saturated or unsaturated and linear or branched $C_8-C_{30}$ acids and of sorbitol;
 saturated or unsaturated oxyethylenated plant oils;
 condensates of ethylene oxide and/or of propylene oxide, inter alia, alone or as mixtures;
 oxyethylenated and/or oxypropylenated silicones.

The surfactants contain a number of moles of ethylene oxide and/or of propylene oxide of between 1 and 100, preferably between 2 and 50 and preferably between 2 and 30. Advantageously, the non-ionic surfactants do not comprise oxypropylene units.

In accordance with a preferred embodiment of the invention, the oxyalkylenated non-ionic surfactants are chosen from oxyethylenated $C_8-C_{30}$ alcohols comprising from 1 to 100 mol of ethylene oxide; and polyoxyethylenated esters of saturated or unsaturated and linear or branched $C_8-C_{30}$ acids and of sorbitol comprising from 1 to 100 mol of ethylene oxide.

As examples of monoglycerolated or polyglycerolated non-ionic surfactants, monoglycerolated or polyglycerolated $C_8-C_{40}$ alcohols are preferably used.

In particular, the monoglycerolated or polyglycerolated $C_8-C_{40}$ alcohols correspond to the formula (A7) below:

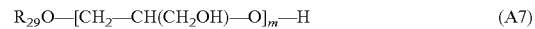

$$R_{29}O-[CH_2-CH(CH_2OH)-O]_m-H \quad (A7)$$

in which formula (A7):
 $R_{29}$ represents a linear or branched $C_8-C_{40}$ and preferably $C_8-C_{30}$ alkyl or alkenyl radical; and
 m represents a number ranging from 1 to 30 and preferably from 1 to 10.

As examples of compounds having the formula (A7) that are suitable within the context of the invention, mention may be made of lauryl alcohol containing 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 oleyl Ether), oleyl alcohol comprising 2 mol of glycerol (INCI name: Polyglyceryl-2 oleyl Ether), cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The alcohol having the formula (A7) may represent a mixture of alcohols in the same way that the value of m represents a statistical value, which means that, in a commercial product, several species of polyglycerolated fatty alcohols may coexist in the form of a mixture.

Use is more preferably made, among the mono- or polyglycerolated alcohols, of the $C_8/C_{10}$ alcohol comprising 1 mol of glycerol, the $C_{10}/C_{12}$ alcohol comprising 1 mol of glycerol and the $C_{12}$ alcohol comprising 1.5 mol of glycerol.

Preferably, the surfactant used in the method of the invention in the composition is a monooxyalkylenated or polyoxyalkylenated, particularly monooxyethylenated or polyoxyethylenated, or monooxypropylenated or polyoxypropylenated, non-ionic surfactant, or their combinations, more particularly monooxyethylenated or polyoxyethylenated.

Preferably, the surfactant(s) is (are) chosen from non-ionic surfactants or from anionic surfactants. More particularly, the surfactant(s) present in the composition is (are) chosen from non-ionic surfactants.

More preferably still, the non-ionic surfactants are chosen from polyoxyethylenated sorbitol esters and polyoxyethylenated fatty alcohols, and their mixtures.

In the composition of the invention, the amount of surfactant(s) in the composition preferably ranges from 0.1% to 50% by weight and better still from 0.5% to 20% by weight relative to the total weight of the composition.

Hair Dyes:

The composition of the invention comprises one or more dyes for keratin fibres whose log P is greater than or equal to 1.3.

This dye or dyes for keratin fibres may be chosen from synthetic or natural dyes.

The synthetic dyes may be chosen from synthetic oxidative dyes and synthetic direct dyes.

The synthetic oxidative dyes may be chosen from oxidation bases and couplers.

Even more preferably, the dye(s) for keratin fibres in the composition of the invention have a log P greater than or equal to 1.5, preferably greater than or equal to 2.

The log P value conventionally represents the partition coefficient of the dye between octanol and water. The log P may be calculated according to the method described in the article by Meylan and Howard "*Atom/fragment contribution method for estimating octanol-water partition coefficient*", J. Pharm. Sci. 84, 83-92 (1995). This value may also be calculated by means of numerous software packages available on the market, which determine the log P as a function of the structure of a molecule. An example that may be mentioned is the Epiwin software from the United States Environmental Agency.

The oxidation bases may be chosen from heterocyclic bases, benzene bases, and their salts.

Among oxidation bases with log P greater than 1.3 mention may be made of 2-n butyl paraphenylene diamine, 2-n pentyl paraphenylene diamine, 4,5-diamino 1-n hexyl pyrazole, 1-ethyl 3-ethyl 4-amino 5-ethylamino pyrazole, 4,5-diamino 1-ethyl 3-(4'-methoxyphenyl)pyrazole.

When they are present, the oxidation base(s) with log P greater than 1.3 according to the invention, each advantageously represent from 0.0001% to 10% by weight relative to the total weight of the composition, and preferably from 0.005% to 5% by weight relative to the total weight of the composition.

The composition of the invention may optionally comprise one or more couplers with log P greater than or equal to 1.3.

Mention may in particular be made, among these couplers, of meta-phenylenediamines, meta-aminophenols, meta-diphenols, naphthalene-based couplers and heterocyclic couplers, and also their addition salts.

As couplers with log P greater than or equal to 1.3, mention may be made of thymol, 2,3,6-trimethylphenol, 5,6,7,8-tetrahydro-1-naphthol, 3,5-dimethoxyphenol, 3-methyl-5-methylphenol, 3,3'-dihydroxybiphenyl, m-o-toluidinophenol, 3,3'-dihydroxydiphenylamine, 8-hydroxyquinoline, 5-hydroxyquinoline, 7-hydroxyquinoline, 2-methyl-1-naphthyl acetate, 2-methyl-1-naphthol, 1,7-dihydroxynaphthalene, 1,6-dihydroxynaphthalene, 3-methyl-indolin-4-ol.

When they are present, the coupler(s) with log P greater than or equal to 1.3 each advantageously represent from 0.0001% to 10% by weight relative to the total weight of the composition and preferably from 0.005% to 5% by weight relative to the total weight of the composition of the invention.

In general, the addition salts of the oxidation bases and couplers that can be used within the context of the invention are especially chosen from the addition salts with an acid such as the hydrochlorides, hydrobromides, sulfates, citrates, succinates, tartrates, lactates, tosylates, benzenesulfonates, phosphates and acetates.

Preferably the oxidative dye with log P greater than or equal to 1.3 is a coupler.

The composition of the invention may additionally comprise one or more synthetic direct dyes with log P greater than or equal to 1.3.

The latter dyes are more particularly chosen from ionic or non-ionic species, preferably non-ionic species. Examples of suitable synthetic direct dyes that may be mentioned include the following direct dyes: azo dyes; methine dyes; carbonyl dyes; azine dyes; nitro(hetero)aryl dyes; tri(hetero)arylmethane dyes; porphyrin dyes and phthalocyanine dyes, alone or as mixtures.

More particularly, the azo dyes comprise an —N═N— function in which the two nitrogen atoms are not simultaneously engaged in a ring. However, it is not excluded for one of the two nitrogen atoms of the sequence —N═N— to be engaged in a ring.

The dyes of the methine family are more particularly compounds comprising at least one sequence chosen from >C═C< and —N═C< in which the two atoms are not simultaneously engaged in a ring. However, it is pointed out that one of the nitrogen or carbon atoms of the sequences may be engaged in a ring. More particularly, the dyes of this family are derived from compounds such as methines, azomethines, monoarylmethanes and diarylmethanes, indoamines (or diphenylamines), indophenols, indoanilines, carbocyanines, azacarbocyanines and their isomers, diazacarbocyanines and their isomers, tetraazacarbocyanines and hemicyanines.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso) violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro(hetero)aromatic dyes are more particularly nitrobenzene or nitropyridine direct dyes.

As regards the dyes of porphyrin or phthalocyaninee type, it is possible to use cationic or non-cationic compounds, optionally comprising one or more metals or metal ions, for instance alkali metals, alkaline-earth metals, zinc and silicon.

Examples of particularly suitable direct dyes that may be mentioned include nitrobenzene dyes; azo direct dyes; azomethine direct dyes; methine direct dyes; azacarbocyanine direct dyes, for instance tetraazacarbocyanines (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes porphyrin direct dyes, alone or as mixtures. In particular, the hydrophobic direct dye(s) with log P greater than or equal to 1.3 may be chosen from the following compounds, alone or as a mixture:

| Dye | Chemical structure |
|---|---|
| Disperse Red 17 | $O_2N$—⟨phenyl⟩—N═N—⟨phenyl(CH_3)⟩—N(CH_2CH_2OH)_2 |

-continued
| Dye | Chemical structure |
|---|---|
| Disperse Violet 1 | 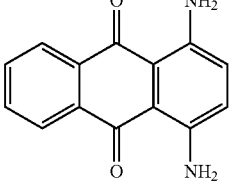 |
| HC Yellow 7 | 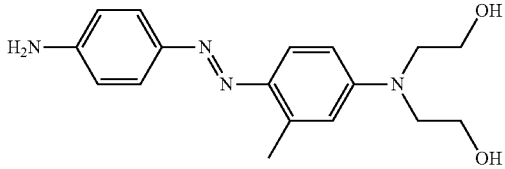 [SMILES: Cc1cc(N(CCO)CCO)ccc1/N=N/c1ccc(N)cc1] |
| Disperse Blue 377 | 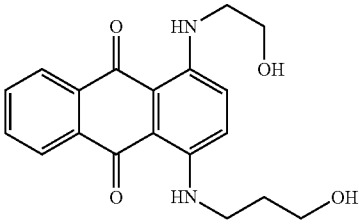 [SMILES: O=C1c2ccccc2C(=O)c2c(NCCCO)ccc(NCCO)c21] |
| Disperse Red 13 | 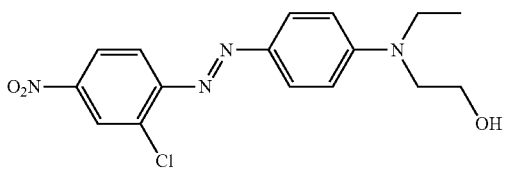 [SMILES: CCN(CCO)c1ccc(/N=N/c2ccc([N+](=O)[O-])cc2Cl)cc1] |
| Disperse Green 9 | 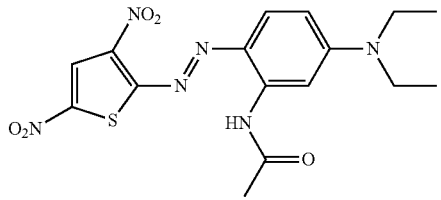 [SMILES: CCN(CC)c1ccc(/N=N/c2sc([N+](=O)[O-])cc2[N+](=O)[O-])c(NC(C)=O)c1] |
| Solvent Black 3 | 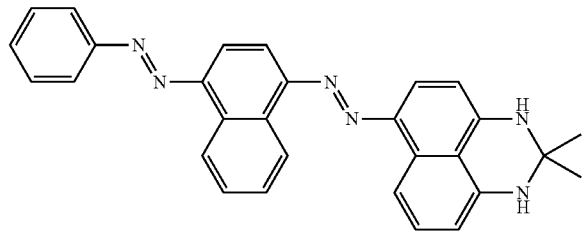 [SMILES: CC1(C)Nc2cccc3c(/N=N/c4ccc(/N=N/c5ccccc5)c5ccccc45)ccc(c23)N1] |
| Disperse Blue 148 | 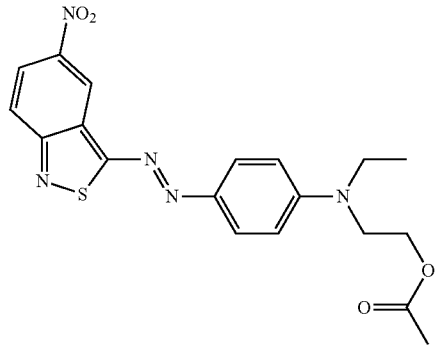 [SMILES: CCN(CCOC(C)=O)c1ccc(/N=N/c2snc3ccc([N+](=O)[O-])cc23)cc1] |

-continued

| Dye | Chemical structure |
|---|---|
| Disperse Violet 63 | 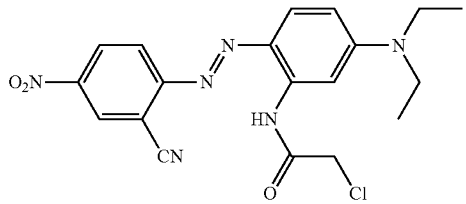 [SMILES: CCN(CC)c1ccc(/N=N/c2ccc([N+](=O)[O-])cc2C#N)c(NC(=O)CCl)c1] |
| Disperse Blue 60 | 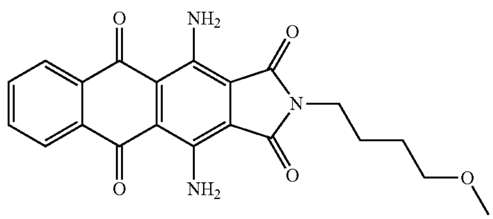 [SMILES: COCCCCn1c(=O)c2c(N)c3c(=O)c4ccccc4c(=O)c3c(N)c2c1=O] |
| Disperse Blue 14 | 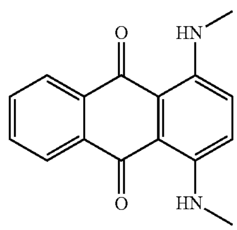 [SMILES: CNc1ccc(NC)c2c1C(=O)c1ccccc1C2=O] |
| Solvent Orange 15 | 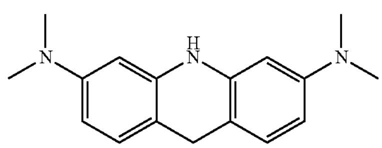 |
| Solvent Orange 7 | 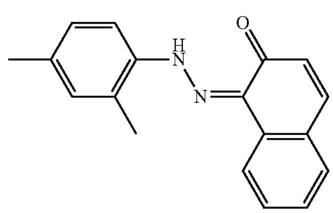 [SMILES: Cc1ccc(N/N=C2\C(=O)C=Cc3ccccc32)c(C)c1] |
| Solvent Blue 14 | 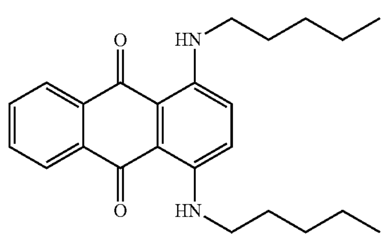 [SMILES: CCCCCNc1ccc(NCCCCC)c2c1C(=O)c1ccccc1C2=O] |
| Disperse Yellow 82 | 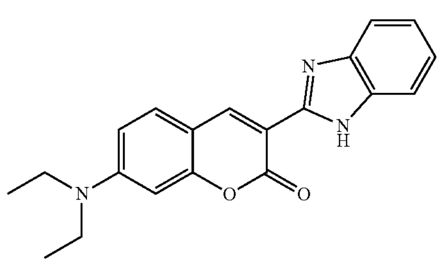 [SMILES: CCN(CC)c1ccc2cc(-c3nc4ccccc4[nH]3)c(=O)oc2c1] |

When they are present, the synthetic direct dye(s) with log P greater than or equal to 1.3 more particularly represent from 0.0001% to 10% by weight, and preferably from 0.005% to 5% by weight, of the total weight of the composition.

Among the natural dyes which may be used according to the invention, mention may be made of indigo, isoindigo, indirubin, isoindirubin, curcumin, apigenidin, orcinol, brasilein, hematein. Extracts or decoctions containing these natural dyes can also be used When they are present, the natural dye(s) with log P greater than or equal to 1.3 more particularly represent from 0.0001% to 10% by weight, and preferably from 0.005% to 5% by weight, of the total weight of the composition.

Preferably, the dye(s) for keratin fibres have a log P greater than or equal to 1.5, preferably greater than or equal to 2.

In a variant, the log P of the dye(s) for keratin fibres varies from 1.3 to 5, preferably from 1.5 to 5, more preferably from 1.5 to 5, most preferably from 2 to 5 and preferentially from 2 to 4.

The compositions of the invention may also comprise one or more additional dyes for fibres having log P below 1.3.

This additional dye(s) may be chosen from synthetic or natural dyes. The additional synthetic dyes may be chosen from synthetic oxidative dyes or synthetic direct dyes.

The synthetic oxidation bases may be chosen from heterocyclic bases, benzene bases, and their salts. The benzene oxidation bases can be more particularly chosen from para-phenylenediamines, bis(phenyl)alkylenediamines, para-aminophenols, ortho-aminophenols, and their addition salts. The heterocyclic bases may be more particularly chosen from pyridine derivatives, pyrimidine derivatives and pyrazole derivatives, and their addition salts.

Among the additional synthetic couplers, mention may be made especially of meta-phenylenediamines, meta-aminophenols, meta-diphenols, naphthalene-based couplers and heterocyclic couplers, and also their addition salts.

The composition of the invention may further optionally comprise one or more synthetic direct dyes. The latter dyes are more particularly chosen from ionic or non-ionic species, preferably cationic or non-ionic species.

Examples of particularly suitable direct dyes that may be mentioned include nitrobenzene dyes; azo direct dyes; azomethine direct dyes; methine direct dyes; azacarbocyanine direct dyes, for instance tetraazacarbocyanines (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes porphyrin direct dyes, alone or as mixtures.

Among the additional natural dyes that can be used according to the invention, mention may be made of lawsone, juglone, alizarin, purpurin, carminic acid, kermesic acid, purpurogallin, protocatechualdehyde, isatin, spinulosin, and orceins. Extracts or decoctions containing these dyes can also be used.

When they are present, the additional dye(s) with log P below 1.3 more particularly represent from 0.0001% to 20% by weight, and preferably from 0.005% to 10% by weight, of the total weight of the composition.

Alkaline Agents:

The composition according to the invention also comprises one or more alkaline agents.

The alkaline agent(s) may be mineral or organic or hybrid.

The mineral alkaline agent(s) are preferably chosen from ammonia, alkali metal carbonates or bicarbonates such as sodium carbonate or bicarbonate, potassium carbonate or bicarbonate, sodium hydroxide or potassium hydroxide, or their mixtures.

The organic alkaline agent(s) are preferably chosen from organic amines with a $pK_b$ at 25° C. of less than 12, preferably less than 10 and even more advantageously less than 6. It should be noted that it is the $pK_b$ corresponding to the functional group of highest basicity. In addition, the organic amines do not comprise any alkyl or alkenyl fatty chains comprising more than ten carbon atoms.

The organic alkaline agent(s) are chosen, for example, from alkanolamines, oxyethylenated and/or oxypropylenated ethylenediamines, amino acids and the compounds having the formula (I) below:

in which formula (I) W is a $C_1$-$C_6$ divalent alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl or $C_1$-$C_6$ hydroxyalkyl or $C_1$-$C_6$ aminoalkyl radical.

Examples of amines having the formula (I) that may be mentioned include 1,3-diaminopropane, 1,3-diamino-2-propanol, spermine and spermidine.

The term "alkanolamine" is intended to mean an organic amine comprising a primary, secondary or tertiary amine function and one or more linear or branched $C_1$-$C_8$ alkyl groups carrying one or more hydroxyl radicals.

Organic amines chosen from alkanolamines such as monoalkanolamines, dialkanolamines or trialkanolamines, comprising one to three identical or different $C_1$-$C_4$ hydroxyalkyl radicals, are in particular suitable for implementing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that can be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that can be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to the following formula (II), and also their salts:

$$R-CH_2-CH{\overset{NH_2}{\underset{CO_2H}{\diagup\diagdown}}} \quad (II)$$

in which formula (II) R represents a group chosen from:

[imidazole structure]; ——(CH$_2$)$_3$NH$_2$; ——(CH$_2$)$_2$NH$_2$;

——(CH$_2$)$_2$NHCONH$_2$; and ——(CH$_2$)$_2$NH—C(=NH)—NH$_2$

The compounds corresponding to formula (II) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that can be used in the present invention, mention may be made especially of carnosine, anserine and balenine.

The organic amine may also be chosen from compounds comprising a guanidine function. As amines of this type that can be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl] amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition of the invention are chosen from alkanolamines, amino acids in neutral or ionic form, in particular basic amino acids, and preferably corresponding to those having the formula (II). More preferably still, the alkaline agent(s) are chosen from monoethanolamine (MEA) and basic amino acids in neutral or ionic form. More preferably, the alkaline agent(s) are chosen from alkanolamines such as monoethanolamine.

Advantageously, the composition according to the invention has a content of alkaline agent(s) ranging from 0.01% to 30% by weight and preferably from 0.1% to 20% by weight relative to the weight of the composition.

According to a first particular embodiment, the composition according to the invention or else the method according to the invention does not use ammonia, or one of its salts, as alkaline agent.

According to a second embodiment, if the composition or if the method according to the invention does use ammonia or one of its salts as alkaline agent, its content should advantageously not exceed 0.03% by weight (expressed as NH$_3$), preferably should not exceed 0.01% by weight, relative to the weight of the composition of the invention.

Preferably, if the composition comprises ammonia, or one of its salts, then the amount of alkaline agent(s) other than the ammonia is greater than that of the ammonia (expressed as NH$_3$).

Chemical Oxidizing Agent:

The composition of the invention comprises one or more chemical oxidizing agents.

The term "chemical oxidizing agent" means an oxidizing agent other than atmospheric oxygen. More particularly, the chemical oxidizing agent(s) are chosen from hydrogen peroxide, urea peroxide, alkali metal bromates, peroxygenated salts, for instance persulfates, perborates, peracids and their precursors, and alkali metal or alkaline-earth metal percarbonates.

This oxidizing agent is advantageously formed from hydrogen peroxide especially in aqueous solution (aqueous hydrogen peroxide solution), the concentration of which may range more particularly from 0.1% to 50% by weight, more preferably still from 0.5% to 20% by weight and better still from 1% to 15% by weight relative to the weight of the composition.

Preferably, the composition of the invention does not contain any peroxygenated salts.

Hydrotropic Compounds:

The composition of the invention comprises at least 0.5% by weight of at least one liquid non-ionic compound having a Hansen parameter $\delta H$ below 16 MPa$^{1/2}$.

Said compounds preferably have Hansen parameters $\delta H$ between 5 and 15.8 MPa$^{1/2}$, more preferably between 8 and 15.8 MPa$^{1/2}$, and most preferably between 8 and 15 MPa$^{1/2}$.

These compounds are liquid at a temperature of 25° C. and at atmospheric pressure (760 mmHg; i.e. 1.013×10$^5$ Pa).

The compound(s) having a Hansen solubility parameter value $\delta H$, as defined previously, are for example, described in the reference publication *Hansen solubility parameters: A User's Handbook* by Charles M. Hansen, CRC Press, 2000, pages 167 to 185, or in the publication *Handbook of Solubility Parameters and Other Cohesion Parameters*, CRC Press, pages 95 to 121 and pages 177 to 185.

This solubility parameter value $\delta H$ is linked to the formation of hydrogen bonds. As a reminder, there are three major types of interactions in organic compounds: non-polar interactions, permanent dipole-dipole interactions and hydrogen bond interactions, the latter being the object of the parameter defining the hydrotropic compound present in the composition used in accordance with the invention.

In particular, the publication *Handbook of Solubility Parameters and Other Cohesion Parameters*, CRC Press, pages 95 to 121 and pages 177 to 185, gives the equation $$\delta H = (\Sigma - {}^z U_h / V)^{1/2}$$

where ${}^z U_h$ (in J·mol$^{-1}$) describes the contributions of the functional group considered in the solubility parameters linked to the hydrogen bonds (values in Table 14, page 183); this parameter ${}^z U_h$ is also described in the publication *The relation between surface tension and solubility parameter in liquids*, Bagda, E, Farbe Lack, 84, 212, 1978;

and V is the volume of the molecule.

It should be noted that the solubility parameter value $\delta H$ is usually given for a temperature of 25° C. and at atmospheric pressure (760 mmHg, i.e. 1.013×10$^5$ Pa).

Said compound(s) can be chosen from:

alcohol ethers, specifically C$_1$-C$_4$ ethers of C$_5$-C$_{30}$ alcohols, preferably saturated, linear or branched, optionally interrupted by one or more non-adjacent ether functions;

aliphatic esters of $C_1$-$C_4$ carboxylic acids and mono- or poly-hydroxylated $C_3$-$C_{10}$ alcohols, interrupted by one or more non-adjacent ether functions;

aromatic ethers, particularly $C_6$-$C_{10}$ aromatic ethers, of $C_1$-$C_6$ alkyl, optionally bearing a hydroxyl group, aryl($C_6$-$C_{10}$)alkyl($C_1$-$C_6$) ethers of $C_1$-$C_6$ alkyl optionally bearing a hydroxyl group, alkanols with aryl substituents, preferably where the aryl portion is $C_6$-$C_{10}$, advantageously $C_6$, and the alkyl portion of the $C_1$-$C_4$ alkanol, where this alkyl portion can be terminated or interrupted by a heteroatom, advantageously oxygen or a hydroxyl group;

lactones preferably having formula (iii), and their mixtures, with:

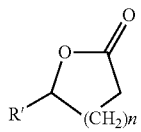

(iii)

in which R' represents a hydrogen, a $C_1$-$C_8$ linear or branched alkyl, a $C_1$-$C_4$ linear or branched hydroxyalkyl, n is 1, 2 or 3 and preferably, R' represents a hydrogen, a $C_1$-$C_6$ linear or branched alkyl, a $C_1$-$C_2$ linear or branched hydroxyalkyl.

As particularly advantageous examples of lactones, mention may be made of γ-butyrolactone.

Preferably, said hydrotropic compound(s) are chosen from alcohol ethers, aliphatic esters, aromatic ethers, alkanols with aryl substituents and their mixtures.

Even more preferentially, said hydrotropic compound(s) are chosen from dipropylene glycol monomethyl ether acetate, dipropylene glycol methyl ether, tripropylene glycol methyl ether, propylene glycol n-butyl ether, propylene glycol n-propyl ether, propylene glycol monomethyl ether, diethylene glycol monomethyl ether and monoethyl ether, 3-phenyl-1-propanol, 2-phenyl-1-propanol, benzyl alcohol, benzyloxyethanol, phenoxyethanol, and mixtures of these compounds.

The liquid compound having a Hansen parameter δH below 16 $MPa^{1/2}$ is even more preferably chosen from alkanols with aryl substituents and most preferably benzyl alcohol.

The liquid compound(s) having a Hansen parameter δH below 16 $MPa^{1/2}$ generally represent from 0.5% to 30% by weight, preferably from 0.5% to 20% by weight, more particularly from 0.5% to 10% by weight, relative to the composition.

Solvent:

The composition according to the invention may also comprise one or more additional different organic solvents for the liquid compounds having a Hansen parameter δH below 16 $MPa^{1/2}$.

Examples of additional organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monoethyl ether and diethylene glycol monomethyl ether, and their mixtures.

The additional solvent(s), if they are present, represent a content usually ranging from 1% to 40% by weight and preferably from 5% to 30% by weight relative to the weight of the composition.

Other Additives:

The composition according to the invention may also contain various adjuvants conventionally used in hair dye compositions, such as anionic, cationic, non-ionic, amphoteric or zwitterionic polymers or their mixtures; mineral thickeners, and in particular fillers such as clays or talc; organic thickeners with, in particular, anionic, cationic, non-ionic and amphoteric polymeric associative thickeners; antioxidants; penetrants; sequestrants; fragrances; dispersants; film-forming agents; ceramides; preservatives; opacifiers.

The above adjuvants are generally present in an amount for each of them of between 0.01% and 20% by weight relative to the weight of the composition.

The composition may especially comprise one or more mineral thickeners chosen from organophilic clays and fumed silicas, or their mixtures.

The organophilic clay may be chosen from montmorillonite, bentonite, hectorite, attapulgite and sepiolite, and their mixtures. The clay is preferably a bentonite or a hectorite.

These clays can be modified with a chemical compound chosen from quaternary ammoniums, tertiary amines, amine acetates, imidazolines, amine soaps, fatty sulfates, alkylarylsulfonates, amine oxides and their mixtures.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The fumed silicas can be obtained by high-temperature pyrolysis of a volatile silicon compound in an oxyhydrogen flame, producing a finely divided silica. This method makes it possible in particular to obtain hydrophilic silicas which exhibit a large number of silanol groups at their surface. Such hydrophilic silicas are sold, for example, under the names Aerosil 130®, Aerosil 200®, Aerosil 255®, Aerosil 300® and Aerosil 380® by the company Degussa, and Cab-O-Sil HS-5®, Cab-O-Sil EH-5®, Cab-O-Sil LM-130®, Cab-O-Sil MS-55® and Cab-O-Sil M-5® by the company Cabot.

It is possible to chemically modify the surface of the silica by chemical reaction for the purpose of reducing the number of silanol groups. It is possible in particular to replace silanol groups with hydrophobic groups: a hydrophobic silica is then obtained.

The hydrophobic groups can be:

trimethylsiloxyl groups, which are obtained in particular by treating fumed silica in the presence of hexamethyldisilazane. Silicas thus treated are known as "Silica silylate" according to the CTFA (6th Edition, 1995). They are sold, for example, under the references Aerosil R812® by the company Degussa, and Cab-O-Sil TS-530® by the company Cabot.

dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th Edition, 1995). They are sold, for example, under the references Aerosil R972® and Aerosil R974® by the company Degussa, and Cab-O-Sil TS-610® and Cab-O-Sil TS-720® by the company Cabot.

The fumed silica preferably exhibits a particle size which can be nanometric to micrometric, for example ranging from approximately 5 to 200 nm.

Preferably, the composition comprises a hectorite, an organomodified bentonite or an optionally modified fumed silica.

When it is present, the inorganic thickener represents from 1% to 30% by weight relative to the weight of the composition.

The composition may also comprise one or more organic thickeners.

These thickeners may be chosen from fatty acid amides (coconut monoethanolamide or diethanolamide, oxyethylenated alkyl ether carboxylic acid monoethanolamide), polymeric thickeners such as cellulose-based thickeners (hydroxyethyl cellulose, hydroxypropyl cellulose or carboxymethyl cellulose), guar gum and their derivatives (hydroxypropyl guar), gums of microbial origin (xanthan gum, scleroglucan gum), crosslinked homopolymers of acrylic acid or of acrylamidopropanesulfonic acid and associative polymers (polymers comprising hydrophilic regions and hydrophobic regions having a fatty chain (alkyl or alkenyl chain comprising at least 10 carbon atoms) that are capable, in an aqueous medium, of reversibly associating with one another or with other molecules).

According to one particular embodiment, the organic thickener is chosen from cellulose-based thickeners (hydroxyethyl cellulose, hydroxypropyl cellulose or carboxymethyl cellulose), guar gum and their derivatives (hydroxypropyl guar), gums of microbial origin (xanthan gum, scleroglucan gum) and crosslinked homopolymers of acrylic acid or of acrylamidopropanesulfonic acid, and preferably from cellulose-based thickeners in particular with hydroxyethyl cellulose.

The content of organic thickener(s), if they are present, usually varies from 0.01% to 20% by weight and preferably from 0.1% to 5% by weight relative to the weight of the composition.

The composition of the invention may be in various forms, for instance a solution, an emulsion (milk or cream) or a gel.

Methods of the Invention:

The composition according to the invention is applied to wet or dry keratin fibres.

It is usually left in place on the fibres for a time generally of from 1 minute to 1 hour and preferably from 5 minutes to 30 minutes.

The temperature during the dyeing method is conventionally between room temperature (between 15° C. and 25° C.) and 80° C., preferably between room temperature and 60° C.

After the treatment, the human keratin fibres are advantageously rinsed with water. They may optionally be washed with a shampoo, followed by rinsing with water, before being dried or left to dry.

The composition according to the invention is generally prepared by mixing at least two compositions, preferably two or three compositions.

In a first variant of the invention, the composition according to the invention results from mixing two compositions. In particular, a composition (A) comprising at least one dye for keratin fibres having a log P greater than or equal to 1.3 and optionally at least one additional dye for keratin fibres and at least one alkaline agent and a composition (B) comprising at least one chemical oxidizing agent are mixed; at least one of compositions (A) and (B) comprising, separately or not, at least one fatty substance, at least one surfactant and/or at least one liquid compound having a Hansen parameter $\delta H$ below 16 $MPa^{1/2}$; the fatty substance content in the composition according to the invention resulting from mixing compositions (A) and (B) comprising at least 25% by weight of fatty substance, the content of liquid compound(s) having a Hansen parameter $\delta H$ below 16 $MPa^{1/2}$ being at least 0.5% by weight relative to the weight of the composition.

At least one of the compositions (A) and (B) is advantageously aqueous.

The expression "aqueous composition" means a composition comprising at least 5% by weight of water, relative to the weight of this composition.

Preferably, an aqueous composition comprises more than 10% by weight of water and more advantageously still more than 20% by weight of water.

Preferably, composition (A) is aqueous. Preferably, composition (B) is also aqueous.

In this variant, composition (A) preferably comprises at least 50% by weight of fatty substances, and more preferably still at least 50% by weight of fatty substances that are liquid at room temperature (25° C.), relative to the weight of this composition (A).

Preferably, composition (A) is a direct emulsion (oil-in-water: O/W) or an inverse emulsion (water-in-oil: W/O), and preferably a direct emulsion (O/W).

In this variant, compositions (A) and (B) are preferably mixed together in a weight ratio (A)/(B) ranging from 0.2 to 10 and better still from 0.5 to 2.

In a second variant of the invention, the composition according to the invention results from mixing three compositions. In particular, the three compositions are aqueous or alternatively at least one of them is anhydrous.

More particularly, for the purposes of the invention, the expression "anhydrous cosmetic composition" means a cosmetic composition with a water content of less than 5% by weight, preferably less than 2% by weight and more preferably still less than 1% by weight relative to the weight of said composition. It should be noted that the water present in the composition is more particularly "bound water", such as the water of crystallization of the salts or traces of water absorbed by the starting materials used in the preparation of the compositions according to the invention.

Preferably, use is made of two aqueous compositions (B') and (C') and one anhydrous composition (A').

The anhydrous composition (A') then preferably comprises at least one fatty substance, and more preferably at least one liquid fatty substance.

The composition (B') then preferably comprises at least one dye for keratin fibres having a log P greater than or equal to 1.3 and optionally at least one additional dye for keratin fibres.

Composition (C') then preferably comprises at least one chemical oxidizing agent.

According to this preferred embodiment of the second variant, the alkaline agent(s) are included in compositions (A') and/or (B') and preferably only in composition (B'). Regarding the surfactant(s) and liquid compound(s) having a Hansen parameter δH below 16 MPa½, these compounds are, separately or not, in at least one of compositions (A'), (B') and (C').

According to this preferred embodiment, the composition according to the invention, i.e. resulting from mixing the three compositions (A'), (B') and (C'), has a fatty substance content of at least 25% by weight of fatty substance, relative to the weight of the composition resulting from the mixing of the three abovementioned compositions.

In this variant, compositions (A'), (B') and (C') are preferably mixed together in a weight ratio [(A')+(B')]/(C') ranging from 0.2 to 10 and more particularly from 0.5 to 2 and in a weight ratio (A')/(B') ranging from 0.5 to 10 and preferably from 1 to 5.

Devices:

Finally, the invention relates to a first multi-compartment device comprising a first compartment containing composition (A) as described above and at least a second compartment containing composition (B) as described above; compositions (A) and (B) of the compartments being intended to be mixed together before application to give a composition according to the invention; the amount of fatty substance of which represents at least 25% by weight relative to the weight of the formulation resulting from mixing compositions (A) and (B).

The invention also relates to a second multi-compartment device comprising a first compartment containing composition (A') as described above and a second compartment containing a cosmetic composition (B') as described above and at least a third compartment comprising composition (C') as described above, the compositions of the compartments being intended to be mixed together before application to give the composition according to the invention; the amount of fatty substance in the composition representing at least 25% by weight relative to the weight of the composition of the invention, i.e. resulting from the mixing of compositions (A'), (B') and (C').

The examples that follow serve to illustrate the invention without, however, being limiting in nature.

EXAMPLES

The following compositions are prepared in which the amounts are expressed in grams of product as is.

Composition A

| | |
|---|---|
| Oxyethylenated lauryl alcohol (2 OE) | 2 |
| Unprotected alkyl (C8/C16) polyglucoside (1.4) in 53% aqueous solution (pH 11.5 to 12.5) | 2 |
| Liquid petrolatum | 78.5 |
| Deionized water | 15 |
| Kaolinite | 1 |
| Hydroxyethyl cellulose (MW: 1 300 000) | 1.5 |

Composition B

| | |
|---|---|
| Propylene glycol | 6.2 |
| Ethyl alcohol | 8.25 |
| Hexylene glycol (2-methyl-2,4-pentanediol) | 3 |
| Dipropylene glycol | 3 |
| Monoethanolamine | 14.5 |
| Sodium metabisulfite | 0.7 |
| Vitamin C: L-ascorbic acid | 0.25 |
| Diethylenetriaminepentaacetic acid, pentasodium salt as a 40% aqueous solution | 1 |
| Hydroxyethyl cellulose (Natrosol 250 HHR, Aqualon) | 3.5 |
| Benzyl alcohol (liquid non-ionic) | 15 |
| Dye (*) | (*) |
| Water | qsp 100 g |

(*) Dyes

| | | |
|---|---|---|
| Composition (1) | Direct Red 17 | 3% |
| Composition (2) | (a): 2-[(3-Aminopyrazolo[1,5-a]pyridin-2-yl)oxy]ethanol hydrochloride | $2 \times 10^{-2}$ mol % |
| | (b): (thymol) | $2 \times 10^{-2}$ mol % |

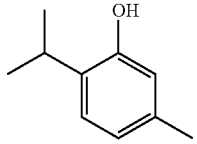

Composition C (Oxidizing Agent)

| | |
|---|---|
| 50% Aqueous hydrogen peroxide solution | 12 |
| Liquid petrolatum | 20 |
| Cetylstearyl alcohol ($C_{16}/C_{18}$ 30/70) | 8 |
| Oxyethylenated cetylstearyl alcohol (33 OE) | 3 |
| Tetrasodium pyrophosphate, $10H_2O$ | 0.03 |
| Disodium tin hexahydrate salt | 0.04 |
| Diethylenetriaminepentaacetic acid, pentasodium salt as a 40% aqueous solution | 0.15 |
| Polydimethyldiallylammonium chloride at 40% in water | 0.5 |
| Poly[(dimethyliminio)-1,3-propanediyl(dimethyliminio)-1,6-hexanediyl dichloride] as a 60% aqueous solution | 0.25 |
| Phosphoric acid | 0 |
| Oxyethylenated rapeseed acid amide (4 EO) | 1.3 |
| Vitamin E | 0.1 |
| Glycerol | 0.5 |
| Deionized water | qsp 100 g |

At the time of use, the following are mixed together (by weight):

10 parts of composition A
4 parts of composition B
15 parts of composition C

The mixture obtained is then applied to locks of natural hair containing 90% grey hairs.

The "mixture/lock" bath ratio is respectively 10/1 (g/g).

The leave-on time is 30 minutes at 27° C.

After this time, the locks are rinsed, and then washed with shampoo and dried.

The colour uptake ($\Delta E_{ab}*$) was evaluated in the CIE L*a* b* system. In this L* a* b* system, L* represents the intensity of the colour, a* indicates the green/red colour axis and b* indicates the blue/yellow colour axis. The lower the value of L*, the darker or more intense the colour.

The value of ΔE* was calculated from the values of L* a* b* according to equation (i) below:

$$\Delta E^* = \sqrt{(L^*-L_o^*)^2+(a^*-a_o)^2+(b^*-b_o^*)^2} \quad \text{(i)}$$

The colour uptake ($\Delta E_{Lab}^*$) was calculated on locks of untreated hair ($L_o^*$, $a_o^*$ and $b_o^*$) and on locks of dyed hair ($L^*$, $a^*$ and $b^*$). The greater the value of ΔE*, the better the coverage of the treated fibres and thus of the roots.

| Composition | L* (D65) | a* (D65) | b* (D65) | ΔE* ab (D65) |
|---|---|---|---|---|
|  | 57.93 | 0.76 | 14.32 | — |
| 1 | 51.17 | 19.12 | 9.58 | 20.13 |
| 2 | 28.32 | 19.11 | 1.52 | 37.11 |

Therefore good colour uptake was observed.

The invention claimed is:

1. A composition for dyeing keratin fibers comprising:
   at least one fatty substance,
   at least one surfactant,
   at least one dye having a log P greater than or equal to 1.3 chosen from thymol, 2,3,6-trimethylphenol, 5,6,7,8-tetrahydro-1-naphthol, 3,5-dimethoxyphenol, 3-methyl-5-methylphenol, 3,3'-dihydroxybiphenyl, m-o-toluidinophenol, 3,3'-dihydroxydiphenylamine, 8-hydroxy-quinoline, 5-hydroxyquinoline, 7-hydroxyquinoline, 2-methyl-1-naphthyl acetate, and 3-methylindolin-4-ol,
   at least one alkaline agent,
   at least one chemical oxidizing agent, and
   at least about 0.5% by weight of at least one liquid non-ionic compound having a Hansen parameter δH less than about 16 $MPa^{1/2}$,
   wherein the composition has a total fatty substance concentration of at least about 25% by weight relative to the total weight of the composition,
   wherein the composition results from mixing at least two sub-compositions,
   wherein a first sub-composition is aqueous and comprises at least one fatty substance, and
   wherein a second sub-composition comprises at least one chemical oxidizing agent.

2. The composition of claim 1, wherein the at least one fatty substance is chosen from $C_6$-$C_{16}$ hydrocarbons, hydrocarbons comprising more than 16 carbon atoms, non-silicone oils of animal origin, vegetable oils of triglyceride type,
   synthetic triglycerides, fluorinated oils, fatty alcohols, fatty acid and/or fatty alcohol esters other than the triglycerides and vegetable waxes, non-silicone waxes, and silicones.

3. The composition of claim 1, wherein the at least one fatty substance is liquid at room temperature and at atmospheric pressure.

4. The composition of claim 1, wherein the at least one fatty substance is chosen from liquid petrolatum, $C_6$-$C_{16}$ alkanes, polydecenes, liquid esters of fatty acids, liquid esters of fatty alcohols, and mixtures thereof.

5. The composition of claim 1, wherein the total concentration of fatty substances ranges from about 25% to about 80% by weight, relative to the total weight of the composition.

6. The composition of claim 1, wherein the at least one surfactant is chosen from non-ionic surfactants.

7. The composition of claim 6, wherein the at least one surfactant is chosen from monooxyalkylenated or polyoxyalkylenated non-ionic surfactants and monoglycerolated or polyglycerolated non-ionic surfactants.

8. The composition of claim 1, wherein the at least one dye has a log P greater than or equal to about 1.5.

9. The composition of claim 1, wherein the at least one liquid non-ionic compound having a Hansen parameter δH less than about 16 $MPa^{1/2}$ is chosen from:
   $C_1$-$C_4$ ethers of $C_5$-$C_{30}$ alcohols, which may be saturated or unsaturated, linear or branched, and optionally interrupted by at least one non-adjacent ether function;
   aliphatic esters of $C_1$-$C_4$ carboxylic acids and mono- or poly-hydroxylated $C_3$-$C_{10}$ alcohols, interrupted by at least one non-adjacent ether function;
   $C_6$-$C_{10}$ aromatic ethers of $C_1$-$C_6$ alkyls, optionally bearing a hydroxyl group,
   aryl($C_6$-$C_{10}$)alkyl($C_1$-$C_6$) ethers of $C_1$-$C_6$ alkyls optionally bearing a hydroxyl group,
   $C_1$-$C_4$ alkanols with $C_6$-$C_{10}$ aryl substituents, the alkyl portion of which can optionally be terminated or interrupted by a heteroatom, and
   lactones of formula (iii), and their mixtures:

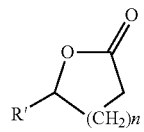

(iii)

in which R' is chosen from hydrogen, $C_1$-$C_8$ linear or branched alkyls, and $C_1$-$C_4$ linear or branched hydroxyalkyls, and n is equal to 1, 2 or 3.

10. The composition of claim 1, wherein the at least one liquid non-ionic compound having a Hansen parameter δH less than about 16 $MPa^{1/2}$ is chosen from dipropylene glycol monomethyl ether acetate, dipropylene glycol methyl ether, tripropylene glycol methyl ether, propylene glycol n-butyl ether, propylene glycol n-propyl ether, propylene glycol monomethyl ether, diethylene glycol monomethyl ether and monoethyl ether, 3-phenyl-1-propanol, 2-phenyl-1-propanol, benzyl alcohol, benzyloxyethanol, phenoxyethanol, and mixtures thereof.

11. The composition of claim 1, wherein the at least one liquid non-ionic compound having a Hansen parameter δH less than about 16 $MPa^{1/2}$ is chosen from $C_1$-$C_4$ alkanols with $C_6$-$C_{10}$ aryl substituents.

12. The composition of claim 1, wherein the at least one liquid compound having a Hansen parameter δH below 16 $MPa^{1/2}$ is present in the composition in an amount ranging from about 0.5% to about 30% by weight, relative to the total weight of the composition.

13. The composition of claim 1, wherein the at least one alkaline agent is a mineral, organic or hybrid alkaline agent chosen from ammonia, alkali metal carbonates and bicarbonates, potassium carbonates and bicarbonates, sodium hydroxide, potassium hydroxide, organic amines, amino acids and compounds of formula (I), and mixtures thereof:

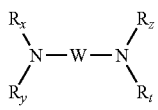

(I)

wherein W is chosen from $C_1$-$C_6$ divalent alkylene radicals optionally substituted with at least one hydroxyl group or $C_1$-$C_6$ alkyl radical, and/or optionally interrupted with at least one heteroatom, and $NR_u$; and $R_x$, $R_y$, $R_z$, $R_t$ and $R_u$, which may be identical or different, are chosen from hydrogen and $C_1$-$C_6$ alkyl, $C_1$-$C_6$ hydroxyalkyl, and $C_1$-$C_6$ aminoalkyl radicals.

14. The composition of claim 13, wherein the at least one alkaline agent is chosen from alkanolamines and amino acids in neutral or ionic form.

15. The composition of claim 1, wherein the at least one chemical oxidizing agent is hydrogen peroxide.

16. A method for dyeing keratin fibers comprising applying to the fibers a composition comprising:
   at least one fatty substance,
   at least one surfactant,
   at least one dye having a log P greater than or equal to 1.3 chosen from thymol, 2,3,6-trimethylphenol, 5,6,7,8-tetrahydro-1-naphthol, 3,5-dimethoxyphenol, 3-methyl-5-methylphenol, 3,3'-dihydroxybiphenyl, m-o-toluidinophenol, 3,3'-dihydroxydiphenylamine, 8-hydroxy-quinoline, 5-hydroxyquinoline, 7-hydroxyquinoline, 2-methyl-1-naphthyl acetate, and 3-methyl-indolin-4-ol,
   at least one alkaline agent,
   at least one chemical oxidizing agent, and
   at least about 0.5% by weight of at least one liquid non-ionic compound having a Hansen parameter δH less than about 16 $MPa^{1/2}$,
   wherein the composition has a total fatty substance concentration of at least about 25% by weight relative to the total weight of the composition,
   wherein the composition results from mixing at least two sub-compositions,
   wherein a first sub-composition is aqueous and comprises at least one fatty substance, and
   wherein a second sub-composition comprises at least one chemical oxidizing agent.

17. The method of claim 16, wherein the composition results from mixing:
   a composition (A) comprising the at least one dye having a log P greater than or equal to 1.3 and the at least one alkaline agent; and
   a composition (B) comprising the at least one chemical oxidizing agent,
   wherein at least one of compositions (A) and (B) comprises, separately or not, the at least one fatty substance, the at least one surfactant and/or the at least one liquid compound having a Hansen parameter δH less than about 16 $MPa^{1/2}$; and
   wherein the total fatty substance content in the composition is at least 25% by weight relative to the total weight of the composition resulting from mixing compositions (A) and (B).

18. The method of claim 16, wherein the composition results from mixing three compositions:
   an anhydrous composition (A') comprising the at least one fatty substance,
   an aqueous composition (B') comprising the at least one dye having a log P greater than or equal to 1.3, and
   an aqueous composition (C') comprising the at least one chemical oxidizing agent,
   wherein at least one of compositions (A') and (B') comprises the at least one alkaline agent,
   wherein at least one of compositions (A'), (B'), and (C') comprises the at least one surfactant and/or the at least one liquid compound having a Hansen parameter δH less than about 16 $MPa^{1/2}$, and
   wherein the fatty substance content in the composition is at least 25% by weight relative to the total weight of the composition resulting from mixing the three compositions (A'), (B') and (C').

19. A multi-compartment device comprising a first compartment containing composition (A) as described in claim 17 and at least a second compartment containing composition (B) as described in claim 17, wherein the compositions of the compartments are mixed together before application to the keratin fibers.

20. A multi-compartment device comprising a first compartment containing composition (A') as described in claim 18, a second compartment containing a cosmetic composition (B') as described in claim 18, and at least a third compartment comprising composition (C') as described in claim 18, wherein the compositions of the compartments are mixed together before application to the keratin fibers.

* * * * *